United States Patent [19]
Welton

[11] Patent Number: 5,415,276
[45] Date of Patent: May 16, 1995

[54] PORTABLE TOOTHPICK HOLDER WITH FLAT TOOTHPICKS

[76] Inventor: B. Robert Welton, 2301 Hollyridge Dr., Los Angeles, Calif. 90068

[21] Appl. No.: 228,411

[22] Filed: Apr. 15, 1994

[51] Int. Cl.⁶ .................... B65D 73/00; B65D 75/00
[52] U.S. Cl. .................................. 206/104; 206/38; 206/63.5; 206/370; 206/37
[58] Field of Search ............... 206/104, 118, 119, 581, 206/370, 820, 823, 443, 38, 37, 63.5

[56] References Cited

U.S. PATENT DOCUMENTS

| | | | |
|---|---|---|---|
| 2,035,425 | 3/1936 | Doll | 206/104 |
| 2,547,252 | 4/1951 | Bouchard et al. | 206/104 |
| 2,547,779 | 4/1951 | Renyck | 206/104 X |
| 3,306,436 | 2/1967 | Diehl | 206/118 |
| 3,438,486 | 4/1969 | Pinkas | 206/104 |
| 3,958,689 | 5/1976 | Roth | 206/104 |
| 5,119,941 | 6/1992 | Lepie | 206/104 X |
| 5,222,510 | 6/1993 | Zuehlsdorf . | |

FOREIGN PATENT DOCUMENTS 9101084 10/1992 Brazil .

OTHER PUBLICATIONS

"PLAC.PIK" device, sold by Prentive Dentistry Products, Inc., P.O. Box 754, Corona del Mar, California.
"STIM-U-DENT" device, sold by Johnson & Johnson Consumer Products, Inc., New Brunswick, N.J. 08903-2400, (800) 526-3967.
Undated Houston Chronicle article on scratch books.

*Primary Examiner*—Jacob K. Ackun
*Attorney, Agent, or Firm*—Pretty, Schroeder, Brueggemann & Clark

[57] ABSTRACT

A toothpick packet having a housing for carrying flat perforated sheets. At least one perforation on each sheet defines a flat toothpick. The housing is selectively openable to allow access to the perforated sheets for the detachment of a toothpick.

16 Claims, 2 Drawing Sheets

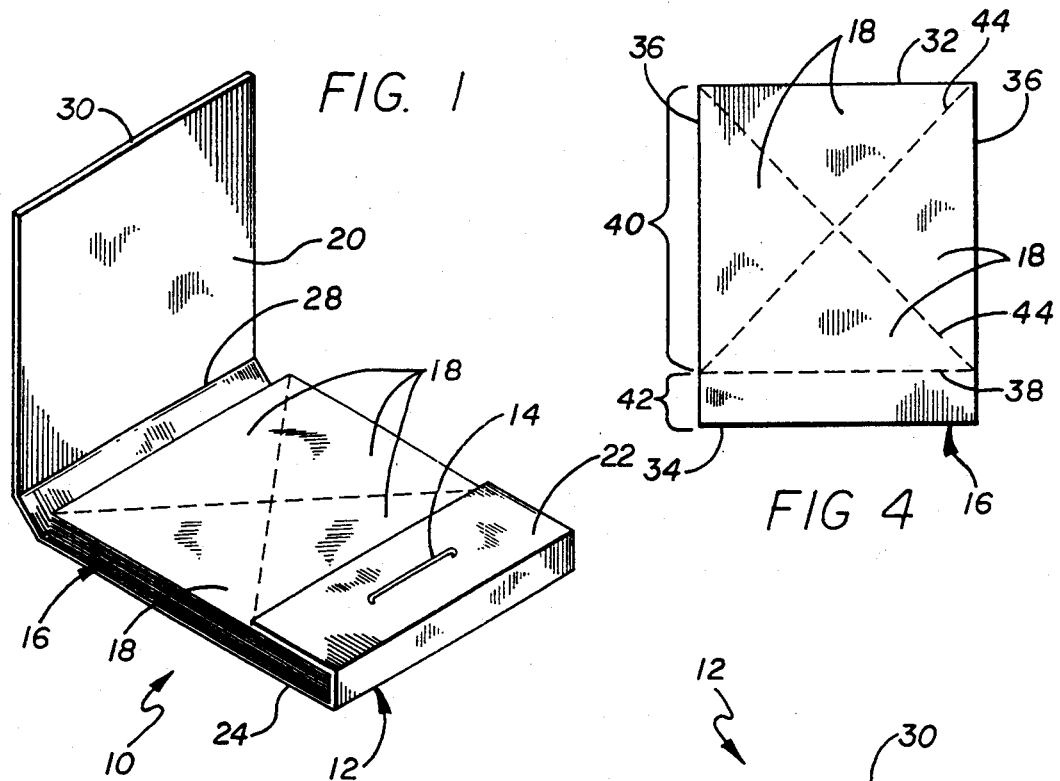
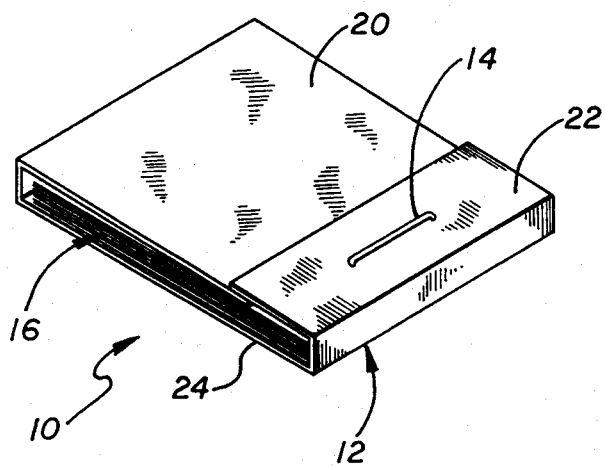
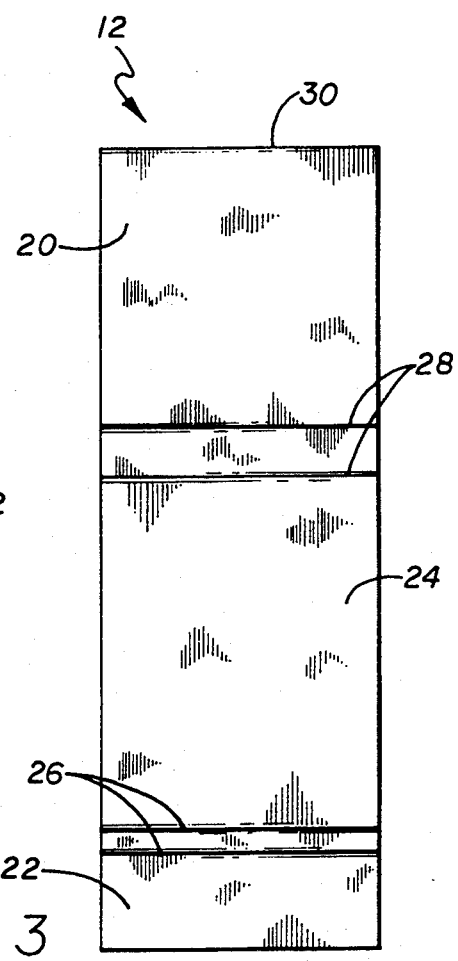

PORTABLE TOOTHPICK HOLDER WITH FLAT TOOTHPICKS

FIELD OF THE INVENTION

The present invention relates to a dental apparatus used to clean teeth, and, more particularly, to a hand-manipulatable implement, or toothpick, for the cleaning of teeth.

BACKGROUND OF THE INVENTION

A toothpick is a device which generally has one or more pointed ends for use in cleaning teeth. A toothpick that is commonly available is disposable and has a generally cylindrical wooden body tapering to two pointed ends. Such disposable wooden toothpicks are inexpensive and very popular. Billions of disposable wooden toothpicks are sold per year and they can be found in most American homes. Due to the huge market for disposable wooden toothpicks, their manufacture has become a very competitive business where manufacturers keep the designs of their toothpick manufacturing equipment as closely guarded secrets. Accordingly, it is relatively difficult for an outsider to start up a company to enter the disposable wooden toothpick market.

One drawback of the common disposable wooden toothpick is the danger of injury from one of its sharply pointed ends. If an accident occurs while a person is using this toothpick, its sharp end can be forced into the user's mouth and cause an injury. Furthermore, depending on the position of the toothpick relative to the user, the sharp ends of the toothpick also can accidentally puncture other parts of the user's body. For example, when the user carries the toothpick in a pocket or a purse, he or she must locate it by touch and risk injury to his or her fingers from the sharp ends of the toothpick. Further, if the toothpick is in a pocket when the user accidentally trips and falls, the resulting impact with the floor could drive the sharp end of the toothpick into the user's flesh.

Another drawback is the inconvenience associated with the handling of the common disposable wooden toothpick. Disposable wooden toothpicks are usually sold in a paper or plastic boxes. These toothpick boxes are relatively weak and generally too large to fit comfortably within a pocket or small purse. Because of the relatively large size of such toothpick boxes, some people put loose toothpicks in their pockets, where they may become soiled, lost, or move into a position whereby they again pose a threat of injury. Further, if such toothpick boxes are placed into a pocket, they may fail when exposed to common torsional and compression loads, thereby releasing the toothpicks from within.

One toothpick packet intended to allow the user to conveniently carry wooden toothpicks has a paper housing capable of carrying 25 wooden toothpicks. The housing carries a rectangular wooden block that is made up of 25 parallel toothpicks joined to each other along their length. When the wooden block is removed from the housing, individual toothpicks can be broken off and used. After being separated from the block, each toothpick is approximately two inches long and is generally triangular in cross-section. Each toothpick has one tapered end for cleaning purposes.

The paper housing has a rectangular pocket along its base to accept the rectangular wooden block. A movable rectangular flap extends upwardly from the rear of the pocket, thereby forming the back side of the packet. The flap is bent to form the upper edge of the packet and also extends back to the front edge of the pocket, thereby forming the front side of the packet. The flap can move between an open position, where the wooden block is removable, and a closed position, where the wooden block is concealed within the housing. The portion of the flap forming the back side of the packet has two side flaps. In the closed position, the side flaps fold around the exposed sides of the wooden block and tuck under the portion of the flap that forms the front side of the packet.

The toothpick packet previously described is generally effective and safe. However, under certain conditions, there may be some drawbacks associated with toothpick packets designed according to this prior art. One drawback is that each toothpick has a tapered end that, if enough force is applied, can injure a user. Another drawback is that the width of each toothpick's tapered end is too great to pass between and clean the teeth of certain individuals.

Yet another drawback is the relatively high expense associated with the production costs and the necessary manufacturing machinery for this toothpick packet. As discussed above, the equipment needed to produce common disposable wooden toothpicks is not available on the open market. Accordingly, anyone wishing to produce toothpicks must design such equipment by trial and error and incur relatively high expenses.

Yet another drawback is associated with the rigidity of the toothpicks which come from the wooden block within the packet. The rigidity of each toothpick may prevent the user from positioning the toothpick at a desired angle within the mouth. During use, a person may desire to clean a crevice between the teeth located near the rear of the mouth. However, the user may be unable to position the end of the toothpick near the rear of the mouth because the rigid body of the toothpick may be obstructed by opposing teeth or cheeks. Accordingly, the access to the rear teeth is limited to positions which are unobstructed, thereby undesirably limiting the cleaning effectiveness of the toothpick.

Another prior toothpick packet includes plastic toothpicks, each having a flexible tip intended to bend and penetrate between the teeth located near the rear of the mouth. The toothpicks are initially joined and form one plastic piece that comes within a closable, envelope-like plastic housing. When the plastic piece is removed from the housing, individual plastic toothpicks can be broken off and used.

The toothpicks from this packet are generally effective in cleaning teeth. However, under certain conditions, several drawbacks may be associated with toothpicks and housings designed according to this prior art. One drawback is that the housing and the toothpicks may be costly to manufacture because they are made of plastic materials.

Another drawback is associated with a relatively sharp edge located on one side of the plastic toothpick. The plastic toothpick is relatively thin to allow for the bending required to clean the teeth located near the rear of the mouth. The thin portion of this plastic toothpick has relatively sharp edges. During use, if too much pressure is applied, this edge can cut the gums of the user.

A final drawback is associated with the loose packaging of the toothpicks within both of the previously described toothpick packets. The wooden block of the first packet and the plastic piece of the second packet are not fastened to their respective housings. Accordingly, during use, the user may position and open each housing in such a way so as to accidentally permit the toothpicks to fall out and become soiled. Furthermore, the user may touch the other toothpicks formed in the wooden block or plastic piece during his or her effort to break off an individual toothpick. Such handling of the other toothpicks may not be sanitary and is undesirable.

It should, therefore, be appreciated that there is still a need for a toothpick packet that has a relatively small housing and toothpicks that are relatively safe, inexpensive, and sanitary. Accordingly, the present invention fulfills these needs.

SUMMARY OF THE INVENTION

The present invention is embodied in a toothpick packet that has a relatively small housing and toothpicks that are relatively safe, inexpensive, and sanitary. More particularly, the present invention is embodied in a toothpick packet having a plurality relatively rigid sheets. Each sheet has one or more perforations that define a plurality of toothpicks. The toothpick packet also has a housing configured to hold the sheets. The housing is moveable between a closed position and an open position. In the closed position, the sheets are positioned within the housing and are not removable from the housing. In the open position, the sheets are removable from the housing.

In another more detailed aspect of the invention, the toothpicks are defined by flat paper sheets made from paper stock having a weight greater than the paper stock used to make standard 10M, 8½ inch×11 inch paper. Each perforated paper sheet is rectangular and has a square portion defined by at least one perforation. The square portion of each sheet has at least two diagonal perforations. Each diagonal perforation is located between the opposite corners of the square portion to define four triangular toothpicks. In another, more detailed feature of the invention, a staple fastens the sheets to the housing.

Because the toothpicks are flat, they are relatively rigid when subjected to compression loads parallel to the plane defined by their flat shape. Accordingly, the toothpicks of the present invention can be constructed of materials previously considered to be too weak for use in conventional toothpick manufacturing, such as paper. Moreover, because the toothpicks are relatively thin, they flex when a force is applied in other directions. Such flexibility advantageously enables the toothpicks to be bent to allow access to the previously hard to reach areas in the rear of the mouth.

An advantage of the present invention is associated with the fastened relationship between the housing and the toothpicks. Because the housing and the toothpicks are fastened together, the toothpicks will not accidently fall out of the housing when it is in the open position. Accordingly, the toothpicks are advantageously kept clean and free of contaminants. Moreover, the toothpicks are more conveniently handled because they will never fall out of the housing.

Another advantage of the flat toothpick of the present invention is that the toothpick is easily handled, even if it has a relatively small size. For example, a small triangular toothpick can be grasped on its flat sides by two fingers, thereby enabling the user to easily position the edges of the toothpick in positions suitable for cleaning all of the teeth, including those near the rear of the mouth.

Such a combination of rigidity and flexibility results in a relatively safer toothpick. Due to the flat shape, the toothpick can have relatively blunt edges. The blunt edges and the flexibility of the toothpick of the present invention facilitate the effective cleaning of the teeth and minimize the risk of accidental injury. If the toothpick of the present invention is accidentally forced towards the gums or other parts of the human body, the blunt edges will resist the creation of a puncture wound. Moreover, the toothpick will probably bend under such accidental loading, thereby advantageously collapsing without causing injury. Furthermore, because the flat sheets are made from paper, they can be easily manufactured according to well known paper industry techniques, thereby avoiding the expense associated with the development of manufacturing machinery for the production of conventional wooden toothpicks.

Other features and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

The following drawings illustrate the preferred embodiments of the invention. In such drawings:

FIG. 1 is a perspective view of a toothpick packet showing an open toothpick housing according to a first embodiment of the present invention;

FIG. 2 is a perspective view of the toothpick packet of FIG. 1, showing the toothpick housing in a closed position;

FIG. 3 is a top view of the toothpick housing of FIG. 1, shown in a flat, unfolded position;

FIG. 4 is a top view of a sheet of toothpicks from the toothpick packet shown in FIG. 1;

DESCRIPTION OF THE PREFERRED EMBODIMENT

Figure 5:
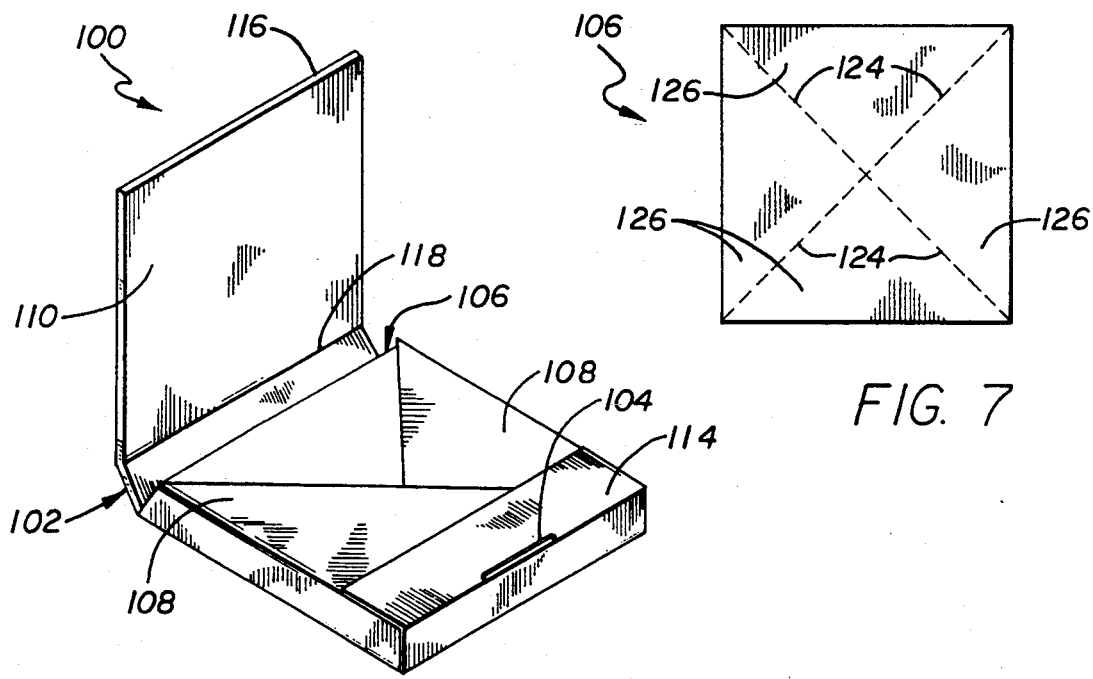
FIG. 5 is a perspective view of a toothpick packet showing an open toothpick housing according to a second embodiment of the present invention.

With reference now to the drawings, and particularly to FIGS. 1-4, there is shown a first embodiment of a toothpick packet 10 in accordance with the present invention. The toothpick packet includes a housing 12, a staple 14, and eight perforated sheets 16 that each contain four detachable triangular toothpicks 18. The housing has a cover 20 that moves between an open position where the toothpicks are removable, as shown in FIG. 1, and a closed position where the toothpicks are not removable, as shown in FIG. 2.

The staple 14 fastens the perforated sheets 16 to the housing 12. The staple can be a standard size commonly used in desk-top stapling machines. However, it is to be understood that the staple can be of any size or type suitable for fastening any given number of perforated sheets together. Furthermore, the proper scope of the invention includes other means for holding the perforated sheets to the housing, such as glue, adhesive, other mechanical fasteners, or any other suitable fastening process.

The toothpick packet 10 has the advantage that the perforated sheets 16 defining the toothpicks 18 will not become accidentally contaminated when the packet is handled. Because the perforated sheets are fastened to the housing 12, the inadvertent spillage and contamination of toothpicks associated with conventional toothpick packets is advantageously avoided.

The housing 12 can be unfolded into a flat, rectangular shape, as shown in FIG. 3. The housing comprises a lower rectangular flap 22, a rectangular back 24 and the generally square cover 20. The housing has two generally parallel horizontal scores 26 between the back and the lower flap. Additionally, two more generally parallel horizontal scores 28 are located between the back and the cover of the housing. The scores 26 and 28 are areas of the housing that have been compressed to facilitate the bending of the housing to form the toothpick packet 10. It should be noted that the word "score" means any physical feature intended to facilitate the bending of the housing, including the compression of the housing.

When the housing is fastened to the perforated sheets 16, the back of the housing is aligned under the perforated sheets. The lower flap and the cover bend 180 degrees and are spaced above the back to rest above the perforated sheets. The cover has an end edge 30 that tucks under the lower flap to hold the housing in the closed position.

The housing 12 is preferably made from paper stock having the same weight as the paper stock used to make 200M, 22½ inch by 28½ inch paper sheets. Such material preferably is double coated to provide a generally smooth finish and also preferably has a varnish coat to prevent any ink on the cover from smearing or running during everyday use. It should be understood that the scope of the invention also includes housings constructed from other suitable materials, including plastic materials.

An individual perforated sheet 16 is shown in FIG. 4. The sheet is rectangular and has an upper edge 32, a lower edge 34, and two side edges 36. A set of horizontal perforations 38 extends between the side edges, parallel to the lower edge. The horizontal perforations are spaced from the upper edge a distance equal to the width of the upper edge, thereby defining a generally square portion 40 between the horizontal perforations and the upper edge of the sheet. A lower portion 42 is defined between the horizontal perforations and the lower edge of the sheet. Two sets of diagonal perforations 44 extend between opposing corners of the square portion, thereby forming triangular toothpicks 18 that can be detached from the perforated sheet.

Preferably, the perforations 38 and 44 are straight slits having a length of approximately 3/32 of an inch and spaced apart approximately 1/32 of an inch. As used herein, the words "perforation" or "perforations" mean any physical feature that enables the user to tear or bend the sheet along a generally predetermined path, including a series of slits or holes formed along the a predetermined path. Further, the words "perforation" or "perforations" also include physical features not including holes, such as a score or a bend.

It should also be understood that, within the proper scope and spirit of the invention, the toothpicks can have any flat shape suitable for cleaning teeth, including square and hexagonal shapes.

Each perforated sheet 16 is preferably made from paper stock having the same weight as the paper stock used to make 240M, 22½ inch×28½ inch paper sheets, but can also be made from any paper or vellum having suitable strength and rigidity, including the paper stock used to make 280M, 22½ inch×28½ inch paper sheets. However, the proper scope of the invention includes perforated sheets made from any relatively rigid material, including wood and plastic materials. To provide effective toothpicks 18 such material should have a rigidity greater than that of a single sheet of the standard 20 pound, 10M paper, 8½-inch ×11-inch size, widely used in office copying machines.

The perforated sheets 16 are vertically stacked so that the horizontal 38 and diagonal 44 perforations of each sheet are vertically aligned with the perforations of the sheets above and below. The staple 14 passes through the lower flap 22 of the housing 12, the lower portion 42 of each sheet, and through the back 24 of the housing. The square portion 40 of a top sheet is exposed when the cover 20 is moved into the open position.

A second embodiment of the invention is shown in FIG. 5. In this embodiment, a toothpick packet 100 includes a housing 102, a staple 104, and eight perforated sheets 106. The housing has two side flaps 108 that wrap around the perforated sheets. The housing also has a cover 110 that moves between an open position where the sheets are removable, as shown in FIG. 5, and a closed position where the sheets are enclosed within the housing.

Figure 6:
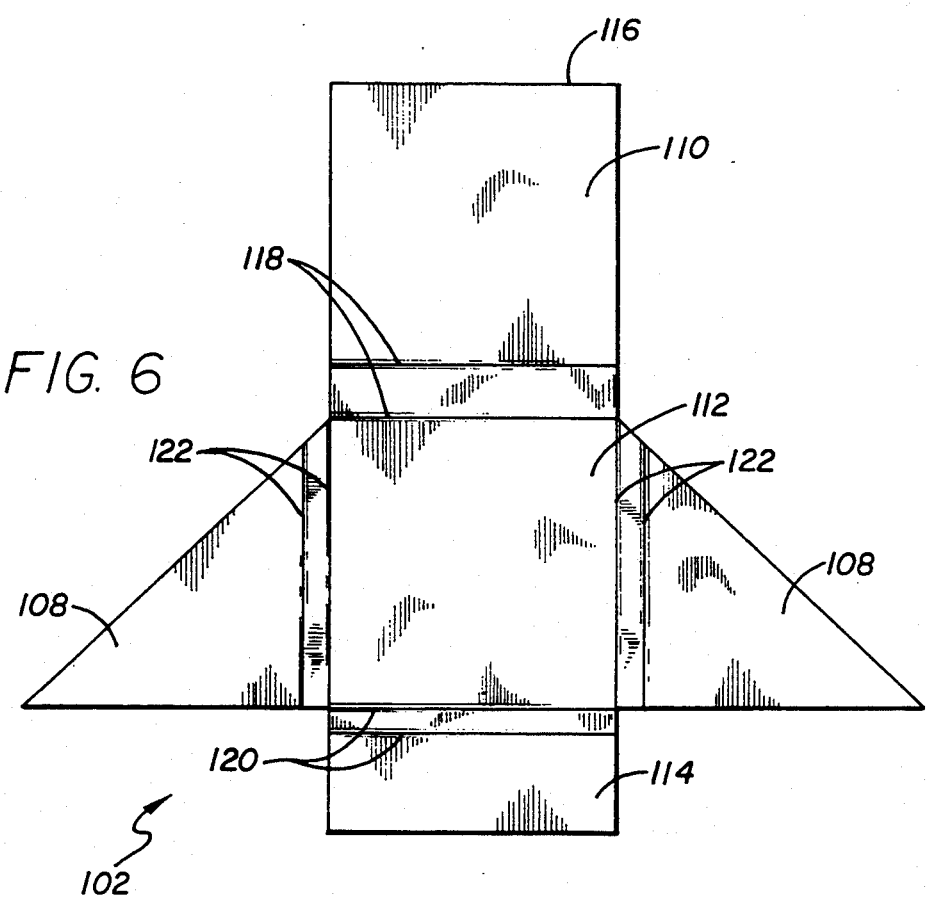
FIG. 6 is a top view of the toothpick housing of FIG. 5, shown in a flat, unfolded position.

As shown in FIG. 6, the housing 102 also has a generally square back 112, and a rectangular lower flap 114. The side flaps of the housing fold around 180° and extend under the lower flap, thereby advantageously preventing dirt and contaminates from soiling the perforated sheets 106. Like the first embodiment of the invention, the cover 110 has an end edge 116 that tucks under the lower flap to hold the housing in the closed position.

The housing 102 has two generally parallel horizontal scores 118 between the back 112 and the cover 110 and two generally parallel horizontal scores 120 between the back and the lower flap 114. Additionally, two generally parallel vertical scores 122 are located on each side flap 108. These vertical scores enable each side flap to bend 180 degrees to a position above the back and under the lower flap and cover of the housing. The side flaps are fastened to the lower flap, thereby forming a pocket to hold the perforated sheets.

The staple 104 holds the side flaps 108 to the lower flap 114 and back 112 of the housing 102. The staple can be of the same type as that of the first embodiment 10 of the invention. However, it is to be understood that the staple can be of any size or type suitable for fastening the side flaps to the lower flap. An alternative method of holding the side flaps to the lower flap is by any suitable adhesive. Furthermore, the proper scope of the invention includes other means for holding the side flaps to the housing, including glue, adhesive, other mechanical fasteners, or any other suitable fastening process.

Figure 7:
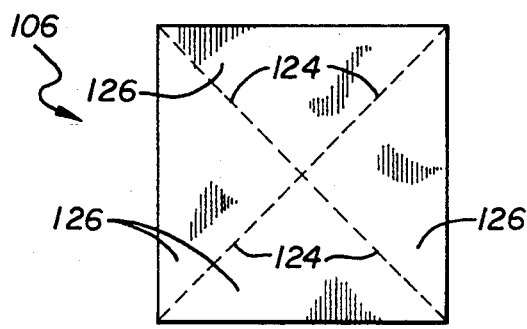
FIG. 7 is a top view of a sheet of toothpicks from the toothpick packet shown in FIG. 5.

One perforated sheet 106 is shown in FIG. 7. The sheet is generally square and has two sets of diagonal perforations 124 extending between its opposing corners, thereby forming four detachable triangular toothpicks 126. The perforated sheet can be made from the same material used to construct the perforated sheet of the first embodiment 10. Further, to maintain the cleanliness of the toothpicks, each perforated sheet can be individually sealed within a wrapper (not shown), made from materials commonly known in the packaging industry.

The toothpick packets 10 and 100 can be inexpensively manufactured using techniques well known in the paper industry. Therefore, the expense associated with the development of manufacturing machinery for the production of conventional wooden toothpicks is advantageously avoided. The toothpick of the present invention can also be impregnated with flavorings or anti-bacterial agents according to well known teachings in the dental arts.

With reference to FIGS. 1 and 2, the function of the first embodiment 10 of the invention will now be described. Initially, the housing 12 is in the closed position. The end edge 30 of the cover 20 is tucked under the lower flap 22, thereby preventing access to the perforated sheets 16. To open the housing, the end edge of the cover is slid out from under the lower flap and the cover is rotated upward to expose the top perforated sheet. A triangular toothpick 18 can then be detached along the perforations of the top sheet. The cover is then tucked under the lower flap so that the housing is again in the closed position. The edges of the toothpick can then be maneuvered across and between the teeth for cleaning purposes.

The relatively thin thickness of the toothpick 18 permits it to clean more effectively between the user's teeth. However, if the user desires a thicker or more rigid toothpick, one piece of the perforated sheet 16 having two triangular sections can be detached and folded over on itself, resulting in a toothpick having the same triangular shape and twice the normal thickness.

The second embodiment of the invention 100 is used in the same manner. However, because the perforated sheets 106 are not fastened to the housing 102, they can slide out when the cover 110 is opened. Accordingly, the user can remove one perforated sheet at a time as new toothpicks are needed. After one perforated sheet is removed, a triangular toothpick can be detached along the perforations 124. The remainder of the perforated sheet is then returned to the housing and the cover is moved into the closed position. The toothpick is used in the same manner as the toothpick 18 of the first toothpick packet 10.

The flat shape of the toothpicks of the present invention represents a great advance over conventional toothpicks. Because of the flat shape, each toothpick is relatively rigid when subjected to compression loads parallel to a plane defined by its triangular shape. Accordingly, the toothpicks of the present invention can be constructed of materials previously considered to be too weak for use in conventional toothpick manufacturing, such as the preferred paper. Moreover, because the toothpicks are relatively thin they flex when force is applied in other directions. Such flexibility enables the toothpicks to bend to allow access to the previously hard to reach areas in the rear of the mouth.

Another advantage of the flat toothpick of the present invention is that the toothpick is easily handled even if it has a relatively small size. For example, a small triangular toothpick can be grasped on its flat sides by two fingers, thereby enabling the user to easily position the edges of the toothpick in positions suitable for cleaning all of the teeth, including those near the rear of the mouth.

The safety of the triangular paper toothpicks 18 and 26 of the present embodiments also represents a great advance over conventional toothpicks. In both embodiments 10 and 100, the toothpick has the rigidity and the thinness necessary to clean teeth, while having relatively blunt edges. The blunt edges and the flexibility of the toothpicks of both embodiments facilitate the effective cleaning of the teeth while minimizing the risk of accidental injury. If the toothpick of the present embodiments is accidentally forced towards the gums or other parts of the human body, the blunt edges will resist the creation of a puncture wound. Moreover, the toothpick will probably bend under such accidental loading, thereby advantageously collapsing without causing injury.

The toothpick packets 10 and 100 are advantageously small, thus they are easily and safely carried within a pocket or purse. Furthermore, the toothpick packets of the present invention can be manufactured relatively inexpensively, as compared with conventional toothpick packets.

It will, of course, be understood that modifications to the present embodiments will be apparent to those skilled in the art. Consequently, the scope of the present invention should not be limited by the particular embodiment discussed above, but should be defined only by the claims set forth below and equivalents thereof.

I claim:

1. A toothpick packet comprising:

a plurality of relatively rigid sheets, each sheet having perforations that define a plurality of toothpicks, and each sheet made from paper stock having a weight greater than the stock used to make standard 10M, 8-½ inch×11 inch size sheets;

wherein the rigid sheets are each rectangular, each sheet having a square portion defined by at least one perforation, the square portion of the sheet having two sets of opposing corners and at least two diagonal perforations, each diagonal perforation extending between a separate one of the sets of the opposing corners to define four triangular toothpicks; and a housing configured to hold the sheets, the housing movable between
 a closed position in which the sheets are positioned within the housing and are not removable from the housing, and
 an open position in which the sheets are removable from the housing.

2. The toothpick packet as defined in claim 1, wherein the toothpicks are impregnated with an anti-bacterial agent.

3. The toothpick packet as defined in claim 1, wherein the toothpicks are impregnated with a flavoring agent.

4. The toothpick packet as defined in claim 1, wherein the sheets are fastened to the housing.

5. The toothpick packet as defined in claim 4, wherein a staple holds the sheets to the housing.

6. The toothpick packet as defined in claim 4, wherein adhesive holds the sheets to the housing.

7. A toothpick packet comprising:

a plurality of relatively rigid rectangular paper sheets, each having a top and a bottom surface, the sheets stacked to collectively define an upper edge, a lower edge, and two side edges, a top surface formed by the uppermost sheet, and a bottom surface formed by the lowermost sheet, each sheet including perforations that define toothpicks, each sheet made from paper stock having a weight greater than the stock used to make standard 10M, 8-½ inch×11 inch size paper, a housing configured to hold the paper sheets, the housing movable between
- a closed position in which the housing extends around the top surface, the lower edge, the bottom surface and the upper edge, and
- an open position in which the top surface of the uppermost sheet is exposed; and a staple positioned adjacent to the lower edge of the stacked sheets and extending through the housing, through the stacked sheets, and through the housing to fasten the sheets to the housing;

wherein each paper sheet has a rectangular portion defined by at least one perforation, the rectangular portion having two sets of opposing corners and at least two diagonal perforations, each diagonal perforation extending between a separate one of the sets of opposing corners to define four triangular toothpicks.

8. The toothpick packet as defined in claim 1, wherein the sheets are separate from the housing.

9. A toothpick packet comprising:

a plurality of paper sheets, each sheet having a generally rectangular portion with two sets of opposing corners and at least one perforation extending between one of the sets of corners, to define a plurality of generally triangular toothpicks; and a housing configured to hold the sheets, the housing movable between
- a closed position in which the sheets are positioned within the housing and are not removable from the housing, and
- an open position in which the sheets are removable from the housing.

10. The toothpick packet as defined in claim 9, wherein the sheets are made from paper stock having a weight greater than the stock used to make standard 10M, 8-½ inch ×11 inch size sheets.

11. The toothpick packet as defined in claim 9, wherein the rectangular portion of each sheet has two perforations each located between one of the opposing sets of corners to define four generally triangular toothpicks.

12. A toothpick packet as defined in claim 9, wherein the toothpicks are impregnated with an antibacterial agent.

13. The toothpick packet as defined in claim 9, wherein the toothpicks are impregnated with a flavoring agent.

14. The toothpick packet as defined in claim 9, wherein the sheets are fastened to the housing.

15. The toothpick packet as defined in claim 13, wherein a staple holds the sheets to the housing.

16. The toothpick packet as defined in claim 9, wherein the sheets are separate from the housing.

* * * * *